US010721963B2

(12) United States Patent
Thorens et al.

(10) Patent No.: US 10,721,963 B2
(45) Date of Patent: Jul. 28, 2020

(54) ELECTRICALLY HEATED AEROSOL DELIVERY SYSTEM

(71) Applicant: PHILIP MORRIS PRODUCTS S.A., Neuchatel (CH)

(72) Inventors: Michel Thorens, Moudon (CH); Olivier Cochand, Dombresson (CH)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 926 days.

(21) Appl. No.: 14/890,465

(22) PCT Filed: May 19, 2014

(86) PCT No.: PCT/EP2014/060225
§ 371 (c)(1),
(2) Date: Nov. 11, 2015

(87) PCT Pub. No.: WO2014/187770
PCT Pub. Date: Nov. 27, 2014

(65) Prior Publication Data
US 2016/0081395 A1 Mar. 24, 2016

(30) Foreign Application Priority Data
May 21, 2013 (EP) .................................... 13168609

(51) Int. Cl.
*A24F 47/00* (2020.01)
*A61M 15/06* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .... A24F 47/008; A24F 47/004; A24F 47/002; A61M 11/042; A61M 15/06; A61M 2205/3653; A61M 2205/8206
See application file for complete search history.

(56) References Cited

U.S. PATENT DOCUMENTS

| 5,388,594 A | 2/1995 | Counts et al. |
| 5,498,855 A | 3/1996 | Deevi et al. |

(Continued)

FOREIGN PATENT DOCUMENTS

| CN | 101116542 A | 2/2008 |
| CN | 101606758 A | 12/2009 |

(Continued)

OTHER PUBLICATIONS

International Search Report and Written Opinion of the International Searching Authority dated Feb. 5, 2015 in PCT/EP2014/060225 filed May 19, 2014.

(Continued)

*Primary Examiner* — Colin W Stuart
*Assistant Examiner* — Douglas Y Sul
(74) *Attorney, Agent, or Firm* — Oblon, McClelland, Maier & Neustadt, L.L.P.

(57) ABSTRACT

An aerosol delivery system for delivering aerosolised medicament particles to a user is provided, including a cartridge and a device configured to receive the cartridge. The cartridge includes a first compartment including a delivery enhancing compound source; a second compartment including a medicament source; a vaporiser configured to heat the medicament; and a transfer element configured to convey the medicament from the second compartment to the vaporiser. The device includes an outer housing; a power source; a temperature controller configured to control the temperature of the first compartment; and electronic circuitry con- (Continued)

Figure 1A:
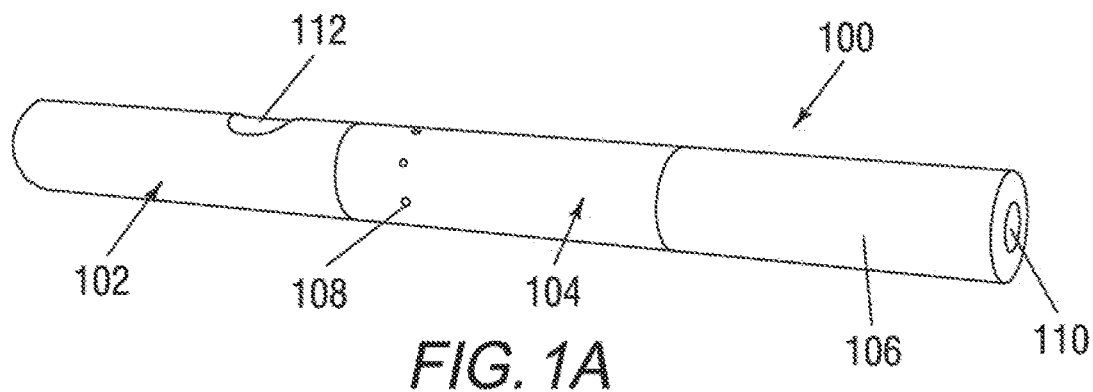

figured to control power to the temperature controller from the power source. The electronic circuitry is configured to maintain the first compartment at a temperature of between about 30° C. and about 50° C.

15 Claims, 2 Drawing Sheets

(51) Int. Cl.
*A61M 11/04* (2006.01)
*F22B 1/28* (2006.01)
*A61M 16/00* (2006.01)

(52) U.S. Cl.
CPC ..... *F22B 1/284* (2013.01); *A61M 2016/0024* (2013.01); *A61M 2205/3653* (2013.01); *A61M 2205/8206* (2013.01); *A61M 2205/8237* (2013.01)

(56) References Cited

U.S. PATENT DOCUMENTS

| | | | |
|---|---|---|---|
| 5,505,214 A | | 4/1996 | Collins et al. |
| 5,514,630 A | | 5/1996 | Willkens et al. |
| 5,591,368 A | | 1/1997 | Fleischhauer et al. |
| 2008/0241255 A1* | | 10/2008 | Rose ................ A61K 31/4439 424/489 |
| 2009/0095311 A1* | | 4/2009 | Han .................... A24F 47/008 131/194 |
| 2009/0272379 A1* | | 11/2009 | Thorens .............. A24F 47/008 128/202.21 |
| 2011/0094523 A1* | | 4/2011 | Thorens .............. A24F 47/008 131/194 |
| 2012/0006342 A1* | | 1/2012 | Rose ................... A24F 47/008 131/273 |

FOREIGN PATENT DOCUMENTS

| | | |
|---|---|---|
| CN | 101878958 A | 11/2010 |
| CN | 102355914 A | 2/2012 |
| CN | 102612361 A | 7/2012 |
| EP | 1 128 741 A1 | 9/2001 |
| EP | 1 736 065 A1 | 12/2006 |
| JP | 2012-520736 A | 9/2012 |
| KZ | 20193 A | 11/2008 |
| KZ | 26743 B | 3/2013 |
| RU | 2 297 781 C2 | 4/2007 |
| WO | WO 00/28843 A1 | 5/2000 |
| WO | WO 03/095688 A2 | 11/2003 |
| WO | WO 2007/066374 A1 | 6/2007 |
| WO | WO 2007/078273 A1 | 7/2007 |
| WO | WO 2008/121610 A1 | 10/2008 |
| WO | WO 2009/132793 A1 | 11/2009 |
| WO | WO 2010/107613 A1 | 9/2010 |
| WO | WO 2011/034723 A1 | 3/2011 |
| WO | WO 2013/030202 A1 | 3/2013 |
| WO | WO 2013/060784 A2 | 5/2013 |

OTHER PUBLICATIONS

Combined Office Action and Search Report dated Dec. 19, 2017 in Chinese Patent Application No. 201480025197.2 (with English language translation), 15 pages.
Written Opinion dated Oct. 27, 2017 in Singaporean Patent Application No. 11201508686U, 7 pages.
"Laboratory Test Chambers for Temperature and Temperature/Humidity Testing the G-8 Elite" Russells Technical Products, http://web.archive.org/web/20120329183105/http://www.russells-tech.com/g-8-elitetest-chamber.htm, Mar. 29, 2012, pp. 1-3.
Office Action dated Mar. 30, 2017 in Kazak Patent Application No. 2015/1444.1 (with English language translation).
Extended Search Report dated Feb. 21, 2014 in European Patent Application No. 13168609.9.
Office Action dated Mar. 5, 2018 in corresponding Japanese Patent Application No. 2016-514355 (with English Translation), 8 pages.

* cited by examiner

ELECTRICALLY HEATED AEROSOL DELIVERY SYSTEM

The invention relates to a cartridge for an aerosol delivery system and to a device configured to receive the cartridge. The invention also relates to an aerosol delivery system for delivering aerosolised medicament, such as nicotine salt particles, to a user comprising a device and a cartridge, in particular to a smoking device for delivering aerosolised nicotine salt particles to a user. The invention further relates to a method of delivering aerosolised medicament, such as nicotine salt particles, to a user.

So-called 'e-cigarettes' and other electrically operated smoking systems that vaporise a liquid nicotine formulation to form an aerosol that is inhaled by a user are known in the art. For example, WO 2009/132793 A1 discloses an electrically heated smoking system comprising a shell and a replaceable mouthpiece wherein the shell comprises an electric power supply and electric circuitry. The mouthpiece comprises a liquid storage portion, a capillary wick having a first end that extends into the liquid storage portion for contact with liquid therein, and a heating element for heating a second end of the capillary wick. In use, liquid is transferred from the liquid storage portion towards the heating element by capillary action in the wick. Liquid at the second end of the wick is vaporised by the heating element. The liquid preferably comprises a tobacco-containing material comprising volatile tobacco flavour compounds which are released from the liquid upon heating.

Commercially available e-cigarettes typically require significant power in order to form an aerosol having suitable particle size for delivery to a user.

WO 2008/121610 A1 and WO 2011/034723 A1 disclose devices and methods for delivering nicotine or other medicaments to a subject in which pyruvic acid is reacted with nicotine or other medicaments in the gas phase to form an aerosol of nicotine, or medicament, pyruvate salt particles. At room temperature both pyruvic acid and nicotine are sufficiently volatile to form respective vapours that react with one another to form nicotine pyruvate salt particles. However, pyruvic acid has a greater vapour pressure than nicotine at a given temperature. As a result, the efficiency of the gas phase reaction between the pyruvic acid and the nicotine is highly dependent on the ambient temperature, which can disadvantageously lead to inconsistent nicotine delivery to a user.

It would be desirable to provide an aerosol delivery system that operates with reduced power consumption as compared to commercially available e-cigarettes. It would also be desirable to provide an aerosol delivery system that allows for more consistent nicotine or other medicament delivery per puff as compared to known devices for delivering aerosolised nicotine salt particles.

According to the invention, there is provided, a cartridge comprising: a first compartment comprising a volatile delivery enhancing compound source; a second compartment comprising a medicament source; a vaporiser for heating the medicament; and a transfer element for conveying the medicament from the second compartment to the vaporiser.

As discussed further below, use of cartridges according to the invention in an aerosol delivery system advantageously allows for more consistent medicament delivery as compared to known devices for delivering aerosolised nicotine, or medicament, salt particles. That is to say, the medicament delivery per puff during use of cartridges according to the invention in an aerosol delivery system is more consistent, than in known devices for delivering aerosolised nicotine, or medicament, salt particles. Furthermore, the medicament delivery per puff during use of cartridges according to the invention in an aerosol delivery system is more constant than in known devices for delivering aerosolised nicotine, or medicament, salt particles.

As used herein, the term "volatile" refers to a delivery enhancing compound having a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

In certain embodiments, the volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

In other embodiments, the volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

In further embodiments, the volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

In yet further embodiments, the volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

In one embodiment, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid.

In a preferred embodiment, the volatile delivery enhancing compound in the first compartment comprises an acid selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. In a particularly preferred embodiment, the first compartment comprises pyruvic acid.

In one embodiment, the volatile delivery enhancing compound comprises ammonium chloride.

In a preferred embodiment, the volatile delivery enhancing compound source comprises a sorption element and a volatile delivery enhancing compound sorbed on the sorption element.

As used herein, by "sorbed" it is meant that the volatile delivery enhancing compound is adsorbed on the surface of the sorption element, or absorbed in the sorption element, or both adsorbed on and absorbed in the sorption element. Preferably, the volatile delivery enhancing compound is adsorbed on the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, the sorption element is a porous sorption element.

For example, the sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

In one preferred embodiment, the sorption element is a substantially cylindrical plug. In one particularly preferred embodiment, the sorption element is a porous substantially cylindrical plug.

In another preferred embodiment, the sorption element is a substantially cylindrical hollow tube. In another particularly preferred embodiment, the sorption element is a porous substantially cylindrical hollow tube.

The size, shape and composition of the sorption element may be chosen to allow a desired amount of volatile delivery enhancing compound to be sorbed on the sorption element.

In a preferred embodiment, between about 20 µl and about 200 µl, more preferably between about 40 µl and about 150 µl, most preferably between about 50 µl and about 100 µl of the volatile delivery enhancing compound is sorbed on the sorption element.

The sorption element advantageously acts as a reservoir for the volatile delivery enhancing compound.

The adsorption element may be configured to convey the volatile delivery enhancing compound from within the first compartment into air drawn through the cartridge. For example, the adsorption element may comprise a capillary material for conveying the volatile delivery enhancing compound from the first compartment into air drawn through the cartridge by capillary action. In certain embodiments, the adsorption element may comprise a capillary wick for conveying the volatile delivery enhancing compound from the first compartment into air drawn through the cartridge by capillary action.

The use of a volatile delivery enhancing compound advantageously allows aerosol delivery systems comprising cartridges according to the invention to operate with reduced power consumption as compared to commercially available e-cigarettes. The power consumption of the aerosol delivery system can be reduced by reducing the power required to vaporise the medicament because the volatile delivery enhancing compound increases the delivery rate of medicament to a user. In contrast, in commercially available e-cigarettes in order to increase the delivery rate of nicotine to a user, additional power is required to vaporise the nicotine formulation to generate smaller aerosol particles. By reducing the power required to generate a suitable aerosol for delivery to a user, the operating temperature of aerosol delivery systems comprising cartridges according to the invention may also be advantageously reduced.

In this way, the invention allows a cost effective, compact and easy to use aerosol delivery system to be provided. Furthermore, by using an acid or ammonium chloride as a delivery enhancing compound in cartridges according to the invention, the pharmacokinetic rate of the medicament as compared to commercially available e-cigarettes may be advantageously increased.

In a preferred embodiment, the cartridge further comprises an aerosol forming chamber in fluid communication with the first compartment and the second compartment. In use, the medicament reacts with the volatile delivery enhancing compound in the gas phase in the aerosol forming chamber to form aerosolised medicament-containing particles.

Preferably, the cartridge further comprises at least one air inlet upstream of the first compartment, and at least one air outlet downstream of the aerosol forming chamber, the at least one air inlet and the at least one air outlet being arranged to define an air flow pathway extending from the at least one air inlet to the at least one air outlet via the first compartment, the vaporiser and the aerosol forming chamber.

As used herein, the terms "upstream" and "downstream" are used to describe the relative positions of components, or portions of components, of cartridges, aerosol delivery devices and aerosol delivery systems according to the invention in relation to the direction of air drawn through the cartridges, aerosol delivery devices and aerosol delivery systems during use thereof.

As used herein, the term "air inlet" is used to describe one or more apertures through which air may be drawn into the cartridge.

As used herein, the term "air outlet" is used to describe one or more apertures through which air may be drawn out of the cartridge.

In a preferred embodiment, the at least one air inlet comprises a plurality of perforations provided in an outer housing of the cartridge. Preferably the perforations extend circumferentially around the outer housing.

Preferably, the medicament has a melting point below about 150 degrees Celsius.

Alternatively or in addition, preferably the medicament has a boiling point below about 300 degrees Celsius.

In certain preferred embodiments, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrhythmic drugs, such as Lidocaine; nicotinic agonists, such as Epibatidine, 5-(2R)-azetidinylmethoxy)-2-chloropyridine (ABT-594), (S)-3-methyl-5-(l-methyl-2-pyrrolidinyl)isoxazole (ABT 418) and (±)-2-(3-Pyridinyl)-1-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

The medicament source is preferably a nicotine source.

The medicament source may comprise a sorption element and a medicament sorbed on the sorption element.

The second compartment may comprise a sorption element with a medicament sorbed thereon. More preferably, the second compartment comprises a porous sorption element with the medicament sorbed thereon. The porous sorption element may comprise one or more porous materials selected from the group consisting of porous plastic materials, porous polymer fibres and porous glass fibres. The one or more porous materials may or may not be capillary materials and are preferably inert with respect to the medicament. The particular preferred porous material or materials will depend on the physical properties of the medicament. The one or more porous materials may have any suitable porosity so as to be used with different medicaments having different physical properties.

Inclusion of a sorption element with a medicament sorbed thereon in the second compartment may advantageously reduce the risk of leakage of the medicament from the cartridge.

Furthermore, by choosing a sorption element having suitable properties, the inclusion of a sorption element may allow improved control of the release of the medicament.

In preferred embodiments, the first compartment of the cartridge comprises a volatile delivery enhancing compound source and the second compartment of the cartridge comprises a nicotine source. The nicotine source may comprise one or more of nicotine, nicotine base, a nicotine salt, such as nicotine-HCl, nicotine-bitartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants. Preferably, the second compartment comprises a liquid medicament source. Preferably, the second compartment is configured to hold between about 50 microlitres and about 150 microlitres of the liquid medicament, more preferably about 100 microlitres of the liquid medicament The liquid medicament has a boiling point suitable for use in an aerosol delivery system as described herein: if the boiling point is too high, the vaporiser will not be able to vaporise the liquid medicament. The liquid medicament also has physical properties that allow the medicament to be conveyed by the transfer element from the second compartment to the vaporiser. Preferably, the liquid medicament has physical properties, including viscosity, that allow the liquid medicament to be conveyed through the transfer element from the second compartment to the vaporiser by capillary action.

The vaporiser is preferably located downstream of the first compartment such that air drawn through the cartridge passes through the first compartment before passing over the vaporiser.

The vaporiser preferably comprises an electrically operated heater, the heater being connectable to an electric power supply. The heater preferably comprises at least one heating element configured to heat the medicament to form a medicament-containing vapour. The heater may comprise a single heating element. Alternatively, the heater may comprise more than one heating element, for example two, three, four, five, six or more heating elements. The heating element or heating elements may be arranged appropriately so as to most effectively vaporise the medicament. The cartridge preferably comprises electrical contacts configured to be coupled to a power source in an aerosol delivery device for providing power to the at least one heating element.

The at least one heating element preferably comprises an electrically resistive material. Suitable electrically resistive materials include but are not limited to: semiconductors such as doped ceramics, electrically 'conductive' ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal and iron-manganese-aluminium based alloys. In composite materials, the electrically resistive material may optionally be embedded in, encapsulated or coated with an insulating material or vice-versa, depending on the kinetics of energy transfer and the external physicochemical properties required. Examples of suitable composite heating elements are disclosed in U.S. Pat. No. 5,498,855, WO 03/095688 A2 and U.S. Pat. No. 5,514,630.

The at least one heating element may take any suitable form. For example, the at least one heating element may take the form of a heating blade, such as those described in U.S. Pat. Nos. 5,388,594, 5,591,368 and 5,505,214. Alternatively, the at least one heating element may take the form of a casing or substrate having different electro-conductive portions, as described in EP 1 128 741 A1, or an electrically resistive metallic tube, as described in WO 2007/066374 A1. Alternatively, the at least one heating element may be a disk (end) heater or a combination of a disk heater with heating needles or rods. Alternatively, the at least one heating element may take the form of a metallic etched foil insulated between two layers of an inert material. In such embodiments, the inert material may comprise Kapton®, all-polyimide or mica foil. Alternatively, the at least one heating element may take the form of a sheet of material, which may be rolled around the vaporiser. The sheet may be made from any suitable material, for example an iron-aluminium based alloy, an iron-manganese-aluminium base alloy or Timetal. The sheet may be rectangular in shape, or may have a patterned shape which may form a coil-like structure when rolled around the vaporiser. Other alternatives include a heating wire or filament, for example a Ni—Cr, platinum, tungsten or alloy wire, such as those described in EP 1 736 065 A1, or a heating plate.

In a preferred embodiment, the at least one heating element comprises a coil of wire surrounding the vaporiser. In that embodiment, preferably the wire is a metal wire. Even more preferably, the wire is a metal alloy wire. The heating element may completely or partially encircle the vaporiser.

In an alternative embodiment, the vaporiser may comprise an atomiser including the at least one heating element. In addition to the heating element, the atomiser may include one or more electromechanical elements such as piezoelectric elements. Additionally or alternatively, the atomiser may also include elements that use electrostatic, electromagnetic or pneumatic effects.

The transfer element may comprise a porous material. The transfer element may have a first portion, which extends into the second compartment, and a second portion adjacent to the vaporiser.

Preferably, the transfer element comprises a capillary material for conveying the medicament from the second compartment to the vaporiser by capillary action. The capillary material may be a capillary wick having a first portion, which extends into the second compartment, and a second portion adjacent to the vaporiser. In use, the medicament is transferred from the second compartment to the vaporiser by capillary action in the capillary wick. When the vaporiser is activated, the medicament in the second portion of the capillary wick is vaporised to form a medicament-containing vapour.

Preferably, the vaporiser is configured to heat the medicament in the second portion of the capillary wick to a temperature of between about 60° C. and about 150° C. More preferably, the vaporiser is configured to heat the medicament in the second portion of the capillary wick to a temperature of between about 65° C. and about 120° C. Yet more preferably, the vaporiser is configured to heat the medicament in the second portion of the capillary wick to a temperature of between about 70° C. and about 100° C. to form a medicament-containing vapour.

The capillary wick may be a linear capillary wick having a first free end extending into the second compartment and a second free end adjacent to the vaporiser. Alternatively, the capillary wick may be a convoluted capillary wick. In such embodiments, the first portion of the capillary wick extending into the vaporiser and the second portion of the capillary wick adjacent to the vaporiser may be free ends of the capillary wick or convoluted portions of the capillary wick. For example, the capillary wick may be a U-shaped capillary wick wherein the curved portion of the U-shaped capillary wick extends into the second compartment and the free ends of the U-shaped capillary wick are adjacent to the vaporiser. Alternatively, the capillary wick may be a U-shaped capillary wick wherein the free ends of the U-shaped capillary wick extend into the second compartment and the curved portion of the U-shaped capillary wick is adjacent to the vaporiser. It will be appreciated that any other suitable shape of capillary wick may also be used.

The capillary wick may have a fibrous or spongy structure. For example, the capillary wick may comprise a plurality of fibres or threads, generally aligned in the longitudinal direction of the cartridge, or sponge-like material formed into a rod shape along the longitudinal direction of the cartridge. The structure of the wick forms a plurality of small bores or tubes, through which the medicament can be transported from the second compartment to the vaporiser, by capillary action. The capillary wick may comprise any suitable material or combination of materials. Examples of suitable materials are ceramic- or graphite-based materials in the form of fibres or sintered powders. The capillary wick may have any suitable capillarity and porosity so as to be used with medicaments having different physical properties such as density, viscosity, surface tension and vapour pressure.

A porous material may be provided between the capillary wick and the vaporiser. The porous material may be any suitable material that is permeable to the medicament and allows the medicament to migrate from the capillary wick to the vaporiser. The porous material is preferably inert with respect to the medicament. The porous material may or may not be a capillary material. The porous material may comprise a hydrophilic material to improve distribution and spread of the medicament. This may assist with consistent vapour formation. The particular preferred material or materials will depend on the physical properties of the medicament. The porous material may have any suitable porosity so as to be used with medicaments having different physical properties. Preferably, the capillary wick and the porous material are in contact, as this provides for good transfer of the medicament.

The at least one heating element may heat the medicament at the second end of the capillary wick by means of conduction. The heating element may be at least partially in contact with the second end of the capillary wick. Alternatively, heat from the heating element may be conducted to the medicament at the second end of the capillary wick by means of a heat conductive element. Alternatively, the at least one heating element may transfer heat to ambient air drawn through the cartridge during use, which in turn heats the medicament at the second end of the capillary wick by convection. The ambient air may be heated before passing over the second end of the capillary wick. Alternatively, the ambient air may be first drawn over the second end of the wick and then heated, as described in WO 2007/078273 A1.

The first compartment comprising the volatile delivery enhancing compound may be provided circumferentially around at least a portion of the second compartment. In such embodiments, the first compartment may be defined by an outer wall of the second compartment and an outer housing of the cartridge. Alternatively, the first compartment and the second compartment may be arranged sequentially along the longitudinal direction of the cartridge with the first compartment upstream from the second compartment. In such embodiments, the first compartment and the second compartment may abut one another or may be spaced apart along the longitudinal direction of the cartridge.

Preferably, the first compartment is substantially sealed prior to first use of the cartridge. For example, the first compartment may comprise one or more seals that may be punctured, or otherwise opened on first use of the cartridge.

As described above, the volatile delivery enhancing compound interacts with the medicament in the gas phase to form medicament-containing particles. Where the volatile delivery enhancing compound is an acid, and the medicament source is a nicotine source, the acid interacts with the nicotine in the gas phase to form nicotine salt particles. Preferably, the Mass Median Aerodynamic Diameter of the nicotine salt particles is less than about 6 microns. The Mass Median Aerodynamic Diameter of the nicotine salt particles may be less than about 1 micron. Preferably, the Mass Median Aerodynamic Diameter of the nicotine salt particles is between about 0.5 microns and about 5 microns.

The cartridge may further comprise a third compartment. Preferably, the third compartment is downstream of the second compartment. Where the cartridge comprises an aerosol forming chamber, the third compartment is preferably downstream of the aerosol forming chamber. The third compartment may comprise a flavour source. Alternatively or in addition, the third component may comprise a filtration material capable of removing at least a portion of any unreacted volatile delivery enhancing compound mixed with aerosolised medicament-containing particles drawn through the third compartment. The filtration material may comprise an adsorbent, such as activated carbon. As will be appreciated, any number of additional compartments may be provided as desired. For example, the cartridge may comprise a third compartment comprising a filter material and a fourth compartment downstream of the third compartment comprising a flavour source.

Preferably, the cartridge comprises an opaque outer housing. This advantageously reduces the risk of degradation of the volatile delivery enhancing compound and medicament due to exposure to light.

According to a further aspect of the invention, there is provided a device configured to receive a cartridge as described herein. The device comprises: an outer housing; a power source; temperature controlling means for controlling the temperature of the first compartment of the cartridge; and electronic circuitry configured to control power to the controlling means from the power source; wherein, the electronic circuitry is configured to maintain the first compartment of the cartridge at a temperature of between about 30° C. and about 50° C.

In a preferred embodiment, the controlling means comprises a heater for heating the first compartment of the cartridge.

The use of such a device in combination with a cartridge according to the invention, advantageously allows for more consistent aerosol generation and medicament delivery per puff. By configuring the device to maintain the first compartment of the cartridge at a temperature of between about 30° C. and about 50° C., the effect of environmental conditions on aerosol generation and medicament delivery per puff can be mitigated.

Alternatively or in addition, the device may comprise a heater for heating ambient air drawn through the device to a temperature of between about 30° C. and about 50° C. before it passes through the first compartment of the cartridge.

According to a yet further aspect of the invention, there is provided an aerosol delivery system. The aerosol delivery system comprises: a device as described herein in cooperation with a cartridge as described herein. The device or cartridge comprises a first compartment comprising a volatile delivery enhancing compound. The device or cartridge comprises a second compartment comprising a medicament source. The device or cartridge comprises a vaporiser for heating the medicament. The device or cartridge further comprises a transfer element for conveying the medicament from the second compartment to the vaporiser. The device or cartridge further comprises an aerosol forming chamber in fluid communication with the first compartment and the second compartment. In use, the medicament reacts with the volatile delivery enhancing compound in the gas phase in the aerosol forming chamber to form aerosolised medicament-containing particles.

Preferably, the device or the cartridge further comprises a mouthpiece in fluid communication with the aerosol forming chamber. Preferably, the mouthpiece is part of the cartridge.

The mouthpiece may comprise any suitable material or combination of materials. Examples of suitable materials include thermoplastics that are suitable for food or pharmaceutical applications, for example polypropylene, polyetheretherketone (PEEK) and polyethylene.

Preferably, the cartridge is not refillable. Thus, when the medicament in the second compartment of the cartridge has been used up, the cartridge is replaced.

In certain embodiments, the device as well as the cartridge may be disposable.

Advantageously, all elements of the device which are potentially in contact with the volatile delivery enhancing compound or the medicament are changed when the cartridge is replaced. This avoids any cross-contamination in the device between different mouthpieces and different cartridges, for example cartridges comprising different volatile delivery enhancing compounds or medicaments.

The medicament in the second compartment may be advantageously protected from exposure to oxygen (because oxygen cannot generally enter the second compartment via the capillary wick or other transfer element) and in some embodiments light, so that the risk of degradation of the medicament is significantly reduced. Therefore, a high level of hygiene can be maintained. Also, the risk of the vaporiser becoming clogged with the medicament may be advantageously significantly reduced by replacing the cartridge at suitable intervals.

In preferred embodiments, the vaporiser comprises an electrically operated heater, the heater being connectable to the power source in the device. When the device and the cartridge are engaged, the heater in the cartridge is in electrical connection with the power supply via the circuitry, the circuitry is arranged to provide power to the heater in the cartridge. In one embodiment, power is provided to the heater in the cartridge when the user activates a switch. In this embodiment, the heater in the cartridge is then provided with substantially continuous power for a fixed period of time. Preferably, the power source has sufficient power to provide power to the heater in the cartridge for at least about 4 minutes, preferably at least about 5 minutes, and more preferably about 6 minutes. It has been found that the average duration of a smoking experience is approximately 6 minutes.

Preferably, the power source comprises sufficient power to enable the user to initiate between about 200 puffs and about 500 puffs.

In an alternative embodiment, power is provided to the heater in the cartridge only when a user initiates a puff. Preferably, the electric circuitry comprises a sensor to detect air flow indicative of a user taking a puff. The sensor may be an electro-mechanical device. Alternatively, the sensor may be any one of: a mechanical device, an optical device, an opto-mechanical device and a micro electro mechanical systems (MEMS) based sensor. In such embodiments, the electronic circuitry is preferably arranged to provide an electric current pulse to the heater in the cartridge when the sensor senses a user taking a puff. Preferably, the time-period of the electric current pulse is pre-set, depending on the amount of nicotine formulation desired to be vaporised. The electronic circuitry is preferably programmable for this purpose.

Alternatively, the electronic circuitry may comprise a manually operable switch for a user to initiate a puff. In such embodiments, the time-period of the electric current pulse sent to the heater in the cartridge upon manual operation of the switch by a user is preferably pre-set depending on the amount of nicotine formulation desired to be vaporised. The electronic circuitry is preferably programmable for this purpose.

Preferably, the power source comprises a cell contained in the device. The power source may be a Lithium-ion battery or one of its variants, for example a Lithium-ion polymer battery. Alternatively, the power source may be a Nickel-metal hydride battery or a Nickel cadmium battery or a fuel cell.

The power source may comprise circuitry chargeable by an external charging portion. In that case, preferably the circuitry, when charged, provides power for a pre-determined number of puffs, after which the circuitry must be re-connected to the external charging portion. An example of suitable circuitry is one or more capacitors or rechargeable batteries.

Preferably, the device and cartridge are arranged to releasably lock together when engaged.

The outer housing of the device may be formed from any suitable material or combination of materials. Examples of suitable materials include, but are not limited to, metals, alloys, plastics or composite materials containing one or more of those materials. Preferably, the outer housing is light and non-brittle.

The aerosol delivery system and device are preferably portable. The system aerosol delivery system may have a size and shape comparable to a conventional smoking article, such as a cigar or cigarette.

According to a yet further aspect of the invention, there is provided a method of delivering aerosolised medicament-containing particles to a user. The method comprises: controlling the temperature of a volatile delivery enhancing compound to between about 30° C. and about 50° C. to form a delivery enhancing compound-containing vapour; heating a medicament source to a temperature of between about 70° C. and about 100° C. form a medicament-containing vapour; and contacting the delivery enhancing compound-containing vapour with the medicament-containing vapour to form aerosolised medicament-containing particles.

In a preferred embodiment, the step of controlling the temperature of the delivery enhancing compound may include heating the delivery enhancing compound.

As will be appreciated, a number of factors influence the formation of the medicament-containing particles. In general, in order to control the medicament delivery it is important to control the vaporisation of the medicament and the volatile delivery enhancing compound. It is also important to control the relative quantities of the medicament and the volatile delivery enhancing compound. In the preferred embodiment, where the volatile delivery enhancing compound is an acid and the medicament source is a nicotine source, the molar ratio of acid to nicotine in the aerosol forming chamber is about 1:1. The use of acid or ammonium chloride as a delivery enhancing compound has been found to approximately double the delivery rate of nicotine to a user for equivalent power supplied to the vaporiser.

The vaporisation of the volatile delivery enhancing compound is controlled by the concentration of the volatile delivery enhancing compound in the first compartment, and by the exchange surface area of volatile delivery enhancing compound in the first compartment. The vaporisation of the volatile delivery enhancing compound may be controlled by heating the first compartment of the cartridge or by heating ambient air drawn through the device before it passes through the first compartment of the cartridge. In preferred embodiments where the first compartment comprises pyruvic acid, preferably about 60 micrograms of pyruvic acid is vaporised per puff.

The vaporisation of the medicament may be controlled through the power supplied to the vaporiser and through the properties of the transfer element for conveying the medicament to the vaporiser.

Preferably, wherein the medicament source is a nicotine source, the power supplied to the vaporiser is between about 0.1 W and about 0.2 W in order to produce an optimal nicotine delivery to the user of about 100 micrograms per puff. More preferably, the power supplied to the heater is between about 0.13 W and about 0.14 W.

In commercial e-cigarettes, the power supplied to the vaporiser is generally much higher; in some cases measurements show a power supply of between about 3.7 W and about 5 W. The reduction in power consumption in aerosol delivery systems and devices according to the invention compared to such e-cigarettes is therefore significant. In addition, the operating temperature of the vaporiser in aerosol delivery systems and cartridges according to the invention can be reduced to between about 80° C. to about 100° C. compared to between about 200° C. to about 300° C. in commercial e-cigarettes.

For the avoidance of doubt, features described above in relation to one aspect of the invention may also be applicable to other aspects of the invention. In particular, features described above in relation to cartridges, devices and aerosol delivery systems according to the invention may also relate, where appropriate to methods according to the invention, and vice versa.

An exemplary embodiment of the invention will now be described with reference to the accompanying drawings in which:

FIGS. 1A-1D show an embodiment of an aerosol delivery system according to the invention; and FIG. 2 shows a detailed view of a cartridge according to an embodiment of the invention without the outer housing.

FIG. 1A shows an aerosol delivery system 100 having the approximate size and shape of a conventional smoking article, such as a cigar or cigarette. The aerosol delivery system 100 comprises a device 102, a cartridge 104 and a mouthpiece 106. The mouthpiece 106 forms part of the cartridge 104. The cartridge 104 comprises air inlets 108 positioned upstream of the mouthpiece, and an air outlet 110 at the mouth-end of the mouthpiece 106. A switch 112 is provided on the device.

Figure 1B:
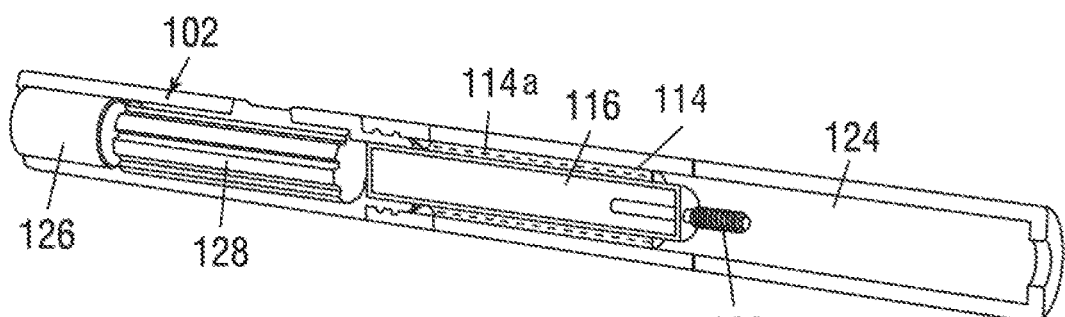

FIG. 1B shows a cross-sectional view of the aerosol delivery system 100, in which further detail of the device 102 and the cartridge 104 is shown. The cartridge 104 comprises a first compartment 114 comprising pyruvic acid and a second compartment 116 comprising a liquid nicotine formulation. As shown in FIG. 1, the first compartment 114 is disposed circumferentially around the second compartment 116 and is defined by the outer circumferential surface of the second compartment 116 and the inner circumferential surface of the outer housing 118 of the cartridge 104.

Figure 1C:
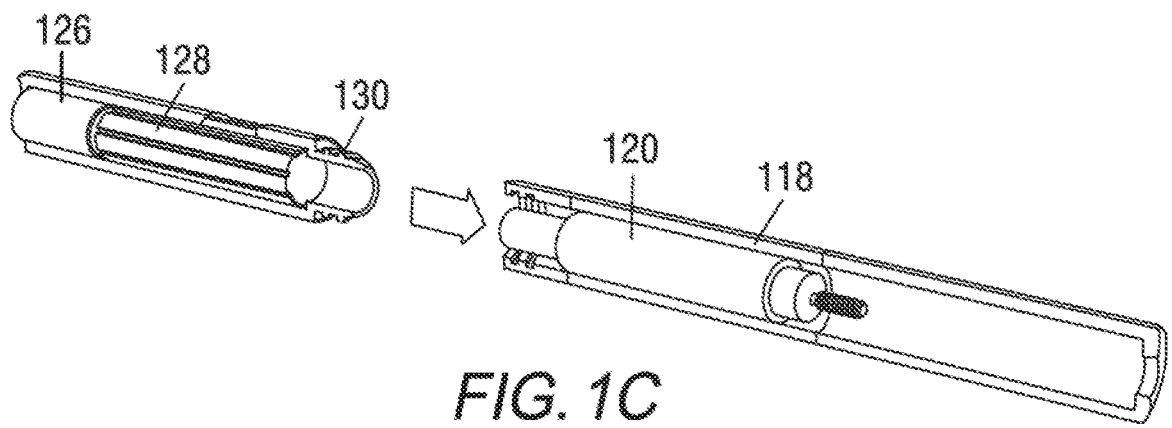

As shown in FIG. 1C, the first compartment 114 comprises a porous plug of fibrous material 120 having pyruvic acid adsorbed thereon. The cartridge 104 further comprises a capillary wick 122 having a first end inside the second compartment 116 and a second end outside the second compartment. The capillary wick 122 is configured to convey the liquid nicotine formulation from the second compartment 116 to a vaporiser surrounding the second end of the capillary wick 122. The vaporiser comprises an electric heater. An aerosol forming chamber 124 is provided downstream of the second compartment 116 in the mouthpiece 106. The mouthpiece 106 may comprise a third compartment (not shown) comprising a filtration material.

The device 102 comprises a power source 126 in the form of a rechargeable battery. The device 102 further comprises electronic circuitry 128 configured to control the supply of power from the power source 126 to the vaporiser. The device 102 also further comprises a heater 114a configured to heat the first compartment 114 of the cartridge 104.

Figure 1D:
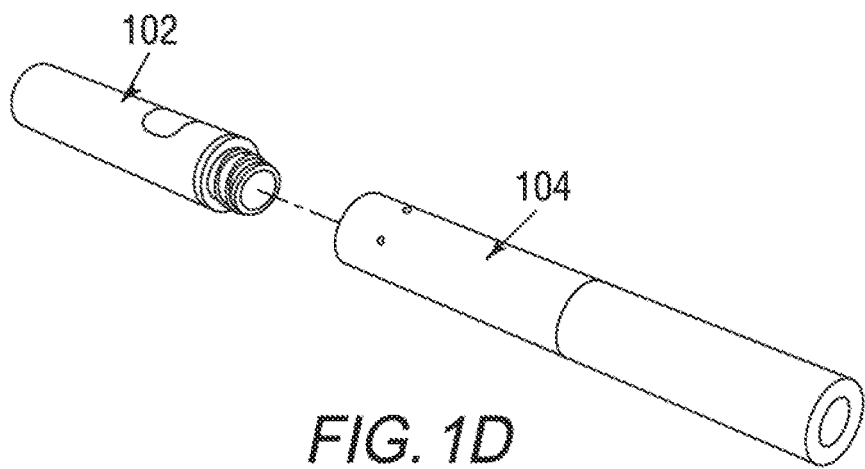

FIG. 1C shows the aerosol delivery system 100 with its component parts separated. The aerosol delivery system 100 is configured such that the cartridge 104 is disposable, and as such may be separated from the device 102, and replaced. A coupling portion 130 is provided to enable the cartridge 104 to be coupled to the device 102. The coupling portion 130 comprises a male threaded portion on the device 102 and a female threaded portion on the cartridge 104. The coupling portion 130 also comprises electrical connectors (not shown) that enable power to be provided to the vaporiser. FIG. 1D shows an alternative view of the aerosol delivery system shown in FIG. 1C.

In use, a user puffs on the mouth-end of the mouthpiece 106, such that air is drawn into the cartridge 104 through the air inlets 108 in the outer housing 118, downstream through the cartridge 104, and then out of the air outlet 110 in the mouthpiece 106 into the user's mouth. The air enters the first compartment 114 and captures a vapour of the pyruvic acid by passing over the porous plug of fibrous material 120 having pyruvic acid adsorbed thereon. To enable consistent pyruvic acid vapour generation, the first compartment is heated by the heater in the device to approximately 40° C. Alternatively, the heater may heat the air drawn into the cartridge 104 through the air inlets 108 in the outer housing 118 before it passes through the first compartment 114. The air stream that exits the first compartment 114 and subsequently passes over the vaporiser is a pyruvic acid-containing air stream.

Puff detection sensors are provided (not shown) that communicate with the electronic circuitry 28. When a puff is sensed, the electronic circuitry activates the vaporiser to vaporise the liquid nicotine formulation. The pyruvic acid-containing air stream and the vaporised nicotine formulation are drawn downstream into the aerosol forming chamber 124. The pyruvic acid and the nicotine interact in the gas phase in the aerosol forming chamber 124 to form nicotine salt particles having a mass median aerodynamic particle diameter of between about 0.5 microns and about 5 microns. The aerosolised nicotine salt particles are drawn out of the cartridge 104 into the mouth of the user through the air outlet 110 in the mouthpiece 106. The aerosol delivery system 100 is configured to deliver approximately 100 micrograms of nicotine to the user per puff. The electronic circuitry is configured to provide approximately 0.14 W of power to the vaporiser for each puff.

Any unreacted pyruvic acid can be removed from the nicotine salt particle aerosol by the filtration material in the third compartment in the mouthpiece 106.

The second compartment 116 is configured to hold approximately 150 microlitres of pyruvic acid, and the second compartment is configured to hold approximately 100 microlitres of the liquid nicotine formulation. The power source 126 is provided with sufficient power to enable approximately 200 to 500 puffs before it is required to be recharged. The volume of the first and second compartments is sufficient to also enable 200 to 500 puffs before the cartridge is required to be replaced. Each puff releases approximately 100 micrograms of nicotine and approximately 60 micrograms of pyruvic acid. In order to optimise the interaction between the nicotine and the pyruvic acid a molar ratio of approximately 1:1 is preferred.

Figure 2:
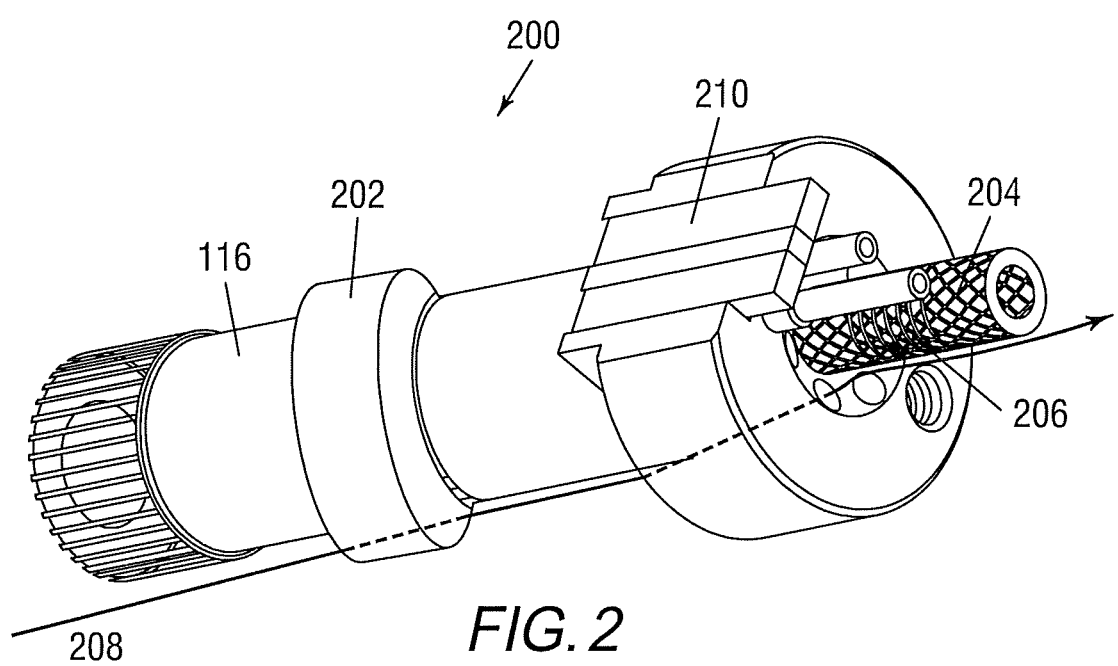

FIG. 2 shows a detailed view of a cartridge 200 comprising the first compartment and second compartment; the configuration shown is an alternative embodiment to that shown in FIGS. 1A-1D. For simplicity, the outer housing of the cartridge has been omitted from FIG. 2. FIG. 2 also shows the airflow pathway through the cartridge. As can be seen, the cartridge 200 comprises a first compartment 202 circumferentially surrounding a portion of the second compartment 116. The second end of the capillary wick 204 is circumscribed by an electric heater 206. The electric heater 206 is in the form of an elongate wire coiled around the capillary wick 204. The arrow 208 shows the airflow pathway from the air inlets through the first compartment 202, and over the capillary wick 204. Electrical contacts 210 are provided to connect the electric heater 206 to the power source in the device (not shown).

Nicotine Discontinuous Heating Example

In order to avoid nicotine losses between puffs, and to simulate a puff detection system, a reference Health Canada smoking regime was applied (puff volume of 55 ml, puff duration of 2 seconds, 30 second interval between puffs) and the signal of the PDSP pump was used to drive the nicotine heating/vaporization through a power supply unit during the 2 s puffs.

In the following experiment, an aerosol delivery system shown in FIG. 1B was prepared. A cartridge including a capillary wick and a heating wire was filled with pure nicotine, while a porous plug (Porex XMF-0507) saturated with 150 μl pyruvic acid was positioned upstream in the puff airflow. Five smoking runs of 30 puffs were completed using increasing heating power from 0 to 0.2W. Deliveries from the groups of 30 puffs were collected on Cambridge filters and analyzed for Nicotine and Pyruvic acid. Results are presented in the table below:

| Heating Power - W | μmol/puff | |
|---|---|---|
| | Nicotine | Pyruvic acid |
| 0 | 0 | 0.28 |
| 0.05 | 0.02 | 0.21 |
| 0.1 | 0.18 | 0.22 |
| 0.15 | 0.62 | 0.36 |
| 0.2 | 0.94 | 0.35 |

As the pyruvic acid plug is not heated (kept at laboratory temperature of 22° C.), the pyruvic acid deliveries are relatively constant, while the nicotine deliveries are increasing as a function of the heating power. In the configuration of the experiment, the optimal equimolar ratio is achieved when nicotine is heated between 0.1 W and 0.15 W.

The experiment confirms that the very low power heating requirement (compared to conventional e-cigarettes) provides the desired amount of ingredients in the aerosol forming chamber for delivery to a consumer.

The invention claimed is:

1. A cartridge, comprising:
   a first compartment comprising a volatile delivery enhancing compound source;
   a second compartment comprising a medicament source;
   a vaporiser configured to heat the medicament; and
   a transfer element configured to convey the medicament from the second compartment to the vaporiser,
   wherein the first compartment comprising the volatile delivery enhancing compound is provided concentrically around at least a portion of the second compartment.

2. The cartridge according to claim 1, further comprising an aerosol forming chamber in fluid communication with the first compartment and the second compartment.

3. The cartridge according to claim 2, further comprising:
   at least one air inlet upstream of the first compartment; and
   at least one air outlet downstream of the aerosol forming chamber,
   the at least one air inlet and the at least one air outlet being configured to define an air flow pathway extending from the at least one air inlet to the at least one air outlet via the first compartment, the vaporiser, and the aerosol forming chamber.

4. The cartridge according to claim 1, wherein the transfer element comprises a capillary material configured to convey the medicament from the second compartment to the vaporiser by capillary action.

5. The cartridge according to claim 4, wherein the capillary material is a capillary wick having a first portion extending into the second compartment and a second portion disposed adjacent to the vaporiser.

6. The cartridge according to claim 1, wherein the second compartment comprises a sorption element with the medicament sorbed thereon.

7. The cartridge according to claim 1, wherein the medicament comprises pure nicotine, a nicotine solution, or a liquid tobacco extract.

8. The cartridge according to claim 1, wherein the first compartment comprises a sorption element with the volatile delivery enhancing compound sorbed thereon.

9. The cartridge according to claim 1, wherein the volatile delivery enhancing compound comprises an acid selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid, and combinations thereof.

10. The cartridge according to claim 1, wherein the vaporiser comprises an electrically operated heater configured to be connected to an electric power supply.

11. A device configured to receive a cartridge according to claim 1, the device comprising:
    an outer housing;
    a power source;
    a first temperature controlling means for controlling a temperature of the first compartment of the cartridge;
    a second temperature controlling means for controlling a temperature of the vaporiser for heating the medicament; and
    electronic circuitry configured to control power to the first and the second temperature controlling means from the power source,
    wherein the electronic circuitry is further configured to maintain the first compartment of the cartridge at a temperature of between about 30° C. and about 50° C.

12. The device according to claim 11, wherein the electronic circuitry is further configured to maintain the temperature of the medicament at a temperature of between about 70° C. and about 100° C.

13. An aerosol delivery system, comprising:
    a device in cooperation with a cartridge, the device or the cartridge comprising
    a first compartment comprising a volatile delivery enhancing compound source;
    a second compartment comprising a medicament source;
    a vaporiser configured to heat the medicament;
    a transfer element configured to convey the medicament from the second compartment to the vaporiser; and
    an aerosol forming chamber in fluid communication with the first compartment and the second compartment,
    wherein the first compartment comprising the volatile delivery enhancing compound is provided concentrically around at least a portion of the second compartment.

14. The aerosol delivery system according to claim 13, wherein the device or the cartridge further comprises a mouthpiece in fluid communication with the aerosol forming chamber.

15. A method of delivering aerosolised medicament-containing particles to a user, the method comprising:
    providing a first compartment comprising a delivery enhancing compound and a second compartment comprising a medicament, the first compartment being provided concentrically around at least a portion of the second compartment;
    controlling a temperature of the delivery enhancing compound to between about 30° C. and about 50° C. to form a delivery enhancing compound-containing vapour;
    heating the medicament to a temperature of between about 70° C. and about 100° C. to form a medicament-containing vapour; and
    contacting the delivery enhancing compound-containing vapour with the medicament-containing vapour to form the aerosolised medicament-containing particles.

* * * * *